(12) United States Patent
Vaezy et al.

(10) Patent No.: US 8,611,189 B2
(45) Date of Patent: Dec. 17, 2013

(54) ACOUSTIC COUPLER USING AN INDEPENDENT WATER PILLOW WITH CIRCULATION FOR COOLING A TRANSDUCER

(75) Inventors: Shahram Vaezy, Seattle, WA (US); Thuc Nghi Nguyen, Olympia, WA (US); Vesna Zderic, Seattle, WA (US); Jessica Foley, Seattle, WA (US)

(73) Assignee: University of Washington Center for Commercialization, Seattle, WA (US)

( * ) Notice: Subject to any disclaimer, the term of this patent is extended or adjusted under 35 U.S.C. 154(b) by 1911 days.

(21) Appl. No.: 11/229,005

(22) Filed: Sep. 16, 2005

(65) Prior Publication Data

US 2006/0235303 A1    Oct. 19, 2006

Related U.S. Application Data

(63) Continuation-in-part of application No. 10/977,339, filed on Oct. 29, 2004, now Pat. No. 7,520,856.

(60) Provisional application No. 60/610,451, filed on Sep. 16, 2004.

(51) Int. Cl.
*B06B 1/00* (2006.01)
*A61B 8/00* (2006.01)

(52) U.S. Cl.
CPC ............... *A61B 8/4281* (2013.01); *A61B 8/546* (2013.01)
USPC .......................................... 367/152; 600/459

(58) Field of Classification Search
USPC ............................ 600/459; 73/644; 367/152
See application file for complete search history.

(56) References Cited

U.S. PATENT DOCUMENTS

| | | | |
|---|---|---|---|
| 385,256 A | 6/1888 | Eggers | |
| 2,992,553 A * | 7/1961 | Joy | ................................ 73/644 |

(Continued)

FOREIGN PATENT DOCUMENTS

| | | | | |
|---|---|---|---|---|
| DE | 04230415 A1 | 3/1994 | ............... | A61B 8/00 |
| EP | 0420758 | 4/1991 | ............... | A61B 8/00 |

(Continued)

OTHER PUBLICATIONS

"Mechanical Bioeffects in the prescence of gas/carrier ultrasound contrast agents." J Ultrasound Med. 19: 120/142, 2000.

(Continued)

*Primary Examiner* — Ian J Lobo
(74) *Attorney, Agent, or Firm* — Perkins Coie, LLP

(57) ABSTRACT

A water pillow for coupling acoustic energy into tissue. The pillow is configured to conform to a transducer to facilitate coupling of ultrasound energy. The pillow includes a pouch that accommodates the transducer to enable a snug fit between the pillow and the transducer. The pillow includes a liquid inlet and outlet to facilitate liquid circulation for cooling, is biocompatible, has a low attenuation, is conformal to the shape of the transducer, facilitates use of an adjustable pressure to achieve various standoffs, includes an integral pouch to facilitate an interference fit to the transducer, facilitates water circulation for cooling, is sterilizable, and is disposable. Either the surface of the pillow adapted to conform to a tissue interface, or the surface of the pillow adapted to conform to the transducer, or both, can include pores configured to weep liquid to facilitate acoustic coupling of the pillow with the transducer and/or tissue.

27 Claims, 8 Drawing Sheets

(56) References Cited

U.S. PATENT DOCUMENTS

| | | | |
|---|---|---|---|
| 4,059,098 A * | 11/1977 | Murdock | 73/644 |
| 4,484,569 A | 11/1984 | Driller et al. | 128/60 |
| 4,545,386 A | 10/1985 | Hetz et al. | 600/462 |
| 4,601,296 A | 7/1986 | Yerushalmi | 607/156 |
| 4,688,578 A * | 8/1987 | Takano et al. | 600/459 |
| 4,708,836 A | 11/1987 | Gain et al. | 264/40.1 |
| 4,773,865 A | 9/1988 | Baldwin | 434/268 |
| RE33,590 E | 5/1991 | Dory | 128/660.03 |
| 5,039,774 A | 8/1991 | Shikinami et al. | 528/60 |
| 5,054,470 A * | 10/1991 | Fry et al. | 601/2 |
| 5,065,742 A | 11/1991 | Belikan et al. | 128/24 |
| 5,080,101 A | 1/1992 | Dory | 128/660.03 |
| 5,080,102 A | 1/1992 | Dory | 128/660.03 |
| 5,088,498 A | 2/1992 | Beach et al. | 600/453 |
| 5,150,712 A | 9/1992 | Dory | 128/660.03 |
| 5,170,790 A | 12/1992 | Lacoste et al. | 600/437 |
| 5,178,148 A | 1/1993 | Lacoste et al. | 600/439 |
| 5,183,046 A | 2/1993 | Beach et al. | 600/453 |
| 5,194,291 A | 3/1993 | D'Aoust et al. | 148/276 |
| 5,215,680 A | 6/1993 | D'Arrigo | 516/11 |
| 5,219,401 A | 6/1993 | Cathignol et al. | 128/660.03 |
| 5,230,334 A | 7/1993 | Klopotek | 128/999.999 |
| 5,289,820 A | 3/1994 | Beach et al. | 600/443 |
| 5,311,869 A | 5/1994 | Okazaki | 128/660.03 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/660.03 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,520,188 A | 5/1996 | Hennige et al. | 128/999.999 |
| 5,522,878 A | 6/1996 | Montecalvo et al. | 607/152 |
| 5,526,815 A | 6/1996 | Granz et al. | 128/660.03 |
| 5,534,232 A | 7/1996 | Denes et al. | 422/186.26 |
| 5,536,489 A | 7/1996 | Lohrmann et al. | 424/9.52 |
| 5,558,092 A | 9/1996 | Unger et al. | 128/660.03 |
| 5,573,497 A | 11/1996 | Chapelon | 601/2 |
| 5,609,485 A | 3/1997 | Bergman et al. | 434/262 |
| 5,638,823 A | 6/1997 | Akay et al. | 600/528 |
| 5,657,760 A | 8/1997 | Ying et al. | 128/999.999 |
| 5,666,954 A | 9/1997 | Chapelon et al. | 600/459 |
| 5,716,374 A | 2/1998 | Francese et al. | 606/207 |
| 5,720,286 A | 2/1998 | Chapelon et al. | 600/439 |
| 5,720,287 A | 2/1998 | Chapelon et al. | 600/439 |
| 5,726,066 A | 3/1998 | Choi | 438/3 |
| 5,755,228 A * | 5/1998 | Wilson et al. | 600/459 |
| 5,762,066 A | 6/1998 | Law et al. | 128/999.999 |
| 5,769,790 A | 6/1998 | Watkins et al. | 600/439 |
| 5,807,285 A | 9/1998 | Vaitekunas et al. | 601/2 |
| 5,810,007 A | 9/1998 | Holupka et al. | 600/439 |
| 5,817,021 A | 10/1998 | Reichenberger | 600/439 |
| 5,823,962 A | 10/1998 | Schaetzle et al. | 600/439 |
| 5,824,277 A | 10/1998 | Campos et al. | 423/242.1 |
| 5,827,204 A | 10/1998 | Grandia et al. | 601/2 |
| 5,833,647 A | 11/1998 | Edwards | 604/22 |
| 5,840,028 A | 11/1998 | Chubachi et al. | 600/437 |
| 5,846,517 A | 12/1998 | Unger | 424/9.52 |
| 5,853,752 A | 12/1998 | Unger et al. | 424/450 |
| 5,873,828 A | 2/1999 | Fujio et al. | 600/439 |
| 5,879,314 E | 3/1999 | Peterson et al. | 601/2 |
| 5,882,302 A | 3/1999 | Driscoll, Jr. et al. | 600/371 |
| 5,895,356 A | 4/1999 | Andrus et al. | 600/439 |
| 5,897,495 A * | 4/1999 | Aida et al. | 600/411 |
| 5,906,580 A | 5/1999 | Kline-Schoder et al. | 600/459 |
| 5,919,139 A | 7/1999 | Lin | 600/443 |
| 5,922,945 A | 7/1999 | Allmaras et al. | 73/52 |
| 5,931,786 A | 8/1999 | Whitmore, III et al. | 600/459 |
| 5,935,339 A | 8/1999 | Henderson et al. | 134/1 |
| 5,951,476 A | 9/1999 | Beach | 600/437 |
| 5,976,092 A | 11/1999 | Chinn | 600/459 |
| 5,993,389 A | 11/1999 | Driscoll, Jr. et al. | 600/371 |
| 5,997,481 A * | 12/1999 | Adams et al. | 600/459 |
| 6,007,499 A | 12/1999 | Martin et al. | 601/3 |
| 6,036,650 A | 3/2000 | Wu et al. | 600/462 |
| 6,039,694 A * | 3/2000 | Larson et al. | 600/459 |
| 6,050,943 A | 4/2000 | Slayton et al. | 600/439 |
| 6,067,371 A | 5/2000 | Gouge et al. | 382/128 |
| 6,071,239 A | 6/2000 | Cribbs et al. | 600/439 |
| 6,128,522 A | 10/2000 | Acker et al. | 600/411 |
| 6,179,831 B1 | 1/2001 | Bliweis | 606/21 |
| 6,200,539 B1 | 3/2001 | Sherman et al. | 422/186.04 |
| 6,221,015 B1 | 4/2001 | Yock | 600/439 |
| 6,267,734 B1 | 7/2001 | Ishibashi et al. | 601/2 |
| 6,406,759 B1 | 6/2002 | Roth | 427/562 |
| 6,409,720 B1 | 6/2002 | Hissong et al. | 606/27 |
| 6,425,867 B1 | 7/2002 | Vaezy et al. | 600/439 |
| 6,443,894 B1 | 9/2002 | Sumanaweera et al. | 600/443 |
| 6,488,639 B1 | 12/2002 | Ribault et al. | 601/2 |
| 6,491,672 B2 | 12/2002 | Slepian et al. | 604/267 |
| 6,548,047 B1 | 4/2003 | Unger | 424/9.51 |
| 6,551,576 B1 | 4/2003 | Unger et al. | 424/9.52 |
| 6,584,360 B2 | 6/2003 | Francischelli et al. | 607/98 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,633,658 B1 | 10/2003 | Dabney et al. | 382/128 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,706,892 B1 | 3/2004 | Ezrin et al. | 548/544 |
| 6,709,407 B2 | 3/2004 | Fatemi | 600/559 |
| 6,716,184 B2 | 4/2004 | Vaezy et al. | 601/3 |
| 6,719,694 B2 | 4/2004 | Weng et al. | 600/439 |
| 6,719,699 B2 | 4/2004 | Smith | 600/459 |
| 6,726,627 B1 | 4/2004 | Lizzi et al. | 600/439 |
| 6,764,488 B1 | 7/2004 | Burbank et al. | 606/51 |
| 6,846,291 B2 | 1/2005 | Smith et al. | 600/459 |
| 6,875,176 B2 | 4/2005 | Mourad et al. | 600/442 |
| 6,875,420 B1 | 4/2005 | Quay | 424/9.52 |
| 6,905,498 B2 | 6/2005 | Hooven | 606/50 |
| 6,955,648 B2 | 10/2005 | Mozayeni et al. | 600/454 |
| 7,149,564 B2 | 12/2006 | Vining et al. | 600/425 |
| 7,260,250 B2 | 8/2007 | Summers et al. | 382/128 |
| 7,491,171 B2 * | 2/2009 | Barthe et al. | 600/439 |
| 7,684,865 B2 | 3/2010 | Aldrich et al. | 607/40 |
| 2002/0016557 A1 | 2/2002 | Duarte et al. | 601/2 |
| 2002/0193681 A1 | 12/2002 | Vitek et al. | 600/411 |
| 2002/0193831 A1 | 12/2002 | Smith, III | 607/2 |
| 2003/0018255 A1 | 1/2003 | Martin et al. | 600/437 |
| 2003/0069569 A1 | 4/2003 | Burdette et al. | 600/427 |
| 2003/0125623 A1 | 7/2003 | Kelly et al. | 600/437 |
| 2003/0144593 A1 | 7/2003 | Whitmore et al. | 600/459 |
| 2003/0195420 A1 | 10/2003 | Mendlein et al. | 600/437 |
| 2003/0208101 A1 | 11/2003 | Cecchi | 600/466 |
| 2004/0002654 A1 | 1/2004 | Davidson et al. | 600/454 |
| 2004/0019278 A1 | 1/2004 | Abend | 600/545 |
| 2004/0030268 A1 | 2/2004 | Weng et al. | 601/2 |
| 2004/0059220 A1 | 3/2004 | Mourad et al. | 600/442 |
| 2004/0059226 A1 | 3/2004 | Peszynski et al. | 600/459 |
| 2004/0078034 A1 | 4/2004 | Acker et al. | 606/27 |
| 2004/0097805 A1 | 5/2004 | Verard et al. | 600/428 |
| 2004/0097840 A1 | 5/2004 | Holmer | 601/2 |
| 2004/0122496 A1 | 6/2004 | Zhang et al. | 600/437 |
| 2004/0143186 A1 | 7/2004 | Anisimov et al. | 600/437 |
| 2004/0153126 A1 | 8/2004 | Okai | 607/1 |
| 2004/0181178 A1 | 9/2004 | Aldrich et al. | 601/3 |
| 2004/0234453 A1 | 11/2004 | Smith | 424/9.5 |
| 2004/0254620 A1 | 12/2004 | Lacoste et al. | 607/96 |
| 2005/0065436 A1 | 3/2005 | Ho et al. | 600/431 |
| 2005/0182319 A1 | 8/2005 | Glossop | 600/424 |
| 2005/0240102 A1 * | 10/2005 | Rachlin et al. | 600/459 |
| 2006/0184069 A1 | 8/2006 | Vaitekunas | 601/2 |
| 2008/0045864 A1 | 2/2008 | Candy et al. | 601/2 |
| 2008/0045865 A1 | 2/2008 | Kislev | 601/3 |
| 2008/0200815 A1 | 8/2008 | Van Der Steen et al. | 600/467 |
| 2008/0319375 A1 | 12/2008 | Hardy | 604/22 |

FOREIGN PATENT DOCUMENTS

| | | | | |
|---|---|---|---|---|
| EP | 01265223 B1 | 11/2002 | | G10K 11/35 |
| JP | H09-103434 | 4/1997 | | A61B 17/36 |
| JP | 2002-500939 | 1/2002 | | A61B 18/00 |

(56) References Cited

FOREIGN PATENT DOCUMENTS

| WO | WO 97/31364 | 8/1997 | ............ G10K 11/02 |
|----|-------------|--------|-------------------------|
| WO | WO 00/72919 | 12/2000 | ............... A61N 7/02 |
| WO | WO 02/069805 | 9/2002 | ............... A61B 8/06 |

OTHER PUBLICATIONS

Bauer, A.; Solbiati, L.; Weissman, N. "Ultrasound Imaging with SonoVue: Low Mechanical Index Real/time Imaging." *Acad Radiol* 2002, 9(suppl 2):S282/S284.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305/1320, 1999. Copyright 1999 World Federation for Ultrasound in Medicine & Biology.

Chen, Wen/Shiang, et al. "A comparison of the fragmentation thresholds and inertial cavitation doses of different ultrasound contrast agents." J. Acoust. Soc. Am. 113 (1), Jan. 2003: pp. 643/651.

Chen, Wen/Shiang, et al. "Inertial Cavitation Dose and Hemolysis Produced in Vitro with or Without Optison." Ultrasound in me. & Biol., vol. 29, No. 5, pp. 725/737, 2003.

Dayton, Paul, A., et al. "The magnitude of radiation force on ultrasound contrast agents." J. Acoust. Soc. Am. 112 (5) Pt. 1, Nov. 2002: pp. 2183/2192.

Everbach, Carr, E. and Charles W. Francis. "Cavitational Mechanisms in Ultrasound/Accelerated Thrombolysis at 1 MHz." Ultrasound in Med. & Biol., vol. 26, No. 7, pp. 1153/1160, 2000. Copyright 2000 World Federation in Medicine and Biology.

Guzman, Hector R., et al. "Ultrasound—Mediated Disruption of Cell Membranes. I. Quantification of Molecular uptake and Cell Viability." J. Acoust. Soc. Am. 110 (1), Jul. 2001: pp. 588/595.

Guzman, Hector R., et al. "Ultrasound/mediated disruption of cell membranes. II. Heterogeneous effects on cells." J. Acoust. Soc. Am 110 (1), Jul. 2001: pp. 597/606.

Holt, Glynn, R., Roy, Ronald, A., Edson, Patrick A., Yang, Xinmai. "Bubbles and Hifu: the Good, the Bad and the Ugly." *Boston University, Department of Aerospace and Mechanical Engineering*, Boston, MA 02215: 120/131.

Hynynen, Kullervo, et al., "Potential Adverse Effects of High/Intensity Focused Ultrasound Exposure on Blood Vessels in Vivo." Ultrasound in Med. & Biol., vol. 22, No. 2, pp. 193/201, 1996.

Indman, Paul, MD,. "Alternatives in Gynecology." Hysteroscopy © 2000 OBGYN.net <http://www.gynalternatives.com/hsc.html>.

Ka/yun Ng, Yang Liu. "Therapeutic Ultrasound: Its Application in Drug Delivery." Medicinal Research Reviews, vol. 22, 204/223, 2002 © 2002 John Wiley & Sons, Inc.

Kaczkowski, Peter J., Vaezy, Shahram, Martin, Roy, Crum, Lawrence. "Development of a High Intensity Focused Ultrasound System for image/guided ultrasonic surgery." Ultrasound for Surgery 2001. <http://cimu.apl.washington.edu/hifusurgerysystem.html>.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." *Acad Radiol* 2002, 9(suppl 2):S279/S281.

Miller, Morton W. et al. "A Review of In Vivo Bioeffects of Interial Ultrasonic Cavitation From a mechanistic Perspective." Ultrasound in Med & Biol., vol. 22, No. 9, pp. 1131/1154, 1996.

Nobuki Kudo, Takehiro Miyaoka, Kengo Okada, and Katsuyuki Yamamoto. "Study on Mechanism of Cell Damage Caused by Microbubbles Exposed to Ultrasound." *Graduate School of Engineering, Hokkaido University, Japan, Research Institute for Electronic Science, Hokkaido University*, 060/0812 Japan.

Ostensen, Jonny, PhD; Bendiksen, Ragner, MSc. "Characterization and Use of Ultrasound Contrast Agents." *Acad Radiol* 2002; 9(suppl 2):S276/S278.

Owaki, T., Nakano, S. Arimura, K., Aikoy, T. "The Ultrasonic Coagulating and Cutting System Injuries Nerve Function." *First Department of Surgery, Kagoshima University School of Medicine*, Kagoshima, Japan, Endoscopy. (2002) 575/579.

Physicians. "Breast Cancer—Insightec: focused ultrasound for non invasive treatment." FAQ <http://www.exablate2000.com/physicians_faq.html>.

Poliachik, Sandra L., et al. "Activation, Aggregation and Ahesion of Platelets Exposed to High/Intensity Focused Ultrasound." Ultrasound in Med. & Biol., vol. 27, No. 11, pp. 1567/1576, 2001.

Poliachik, Sandra L., et al. "Effect of High—Intensity Focused Ultrasound on Whole Blood with or without Microbubble Contrast Agent." Ultrasound in Med. & Biol., vol. 25, No. 6, 1999: 991/998.

Porter, T.R., Xie, F. "Ultrasound, Microbubbles and Thrombolysis." Progress in Cardiovascular Diseases, vol. 44, No. 2, Oct. 2001: 101/110.

Rivens, I.H., Rowland, I.J., Denbow, M., Fisk, N.M., Harr, G.R., Leach, M.O. "Vascular occlusion using focused ultrasound surgery for use in fetal medicine." *European Journal of Ultrasound 9 (1999)*: 89/97.

Rosenschein, Uri, et al. "Ultrasound Imaging/Guided Nonivasive Ultrasound Thrombolysis/Preclinical Results." © 2000 American Heart Association, Inc. (Circulation. 2000;102:238/245.) <http://www.circulationaha.com.org>.

Rosenschein, Uri, et al. "Shock/Wave Thrombus Ablation, A New Method for Noninvasive Mechanical Thrombolysis." The American Journal of Cardiology, vol. 70, Issue 15, Nov. 1992: pp. 1358/1361.

Tachibana, Katsuro and Shunro MD., PhD. "The Use of Ultrasound for Drug Delivery." *First Department of Anatomy, Fukuoka University School of Medicine*, Nanakuma, Japan,Echocardiography. (2001) 323/328.

Tachibana, Katsuro, and Shunro M.D., Ph.D., "Albumin Microbubble Echo/Contrast Material as an Enhancer for Ultrasound Accelerated Thrombolysis." (Circulation, 1995; 92: 1148/1150.) © 1995 American Heart Association, Inc.

Tardy, I; Pochon, S.; Theraulaz, P. Nanjappan; Schneider, M., "In Vivo Ultrasound Imaging of Thrombi Using a Target/specific Contrast Agent[1]." *Acad Radiol* 2002, 9(suppl 2):S294/S296.

Vaezy, Shahram et al., 2001. "Acoustic surgery." *Physics World* (August): 35/39.

Vaezy, Shahram et al. 2001. "Experimental Investigation and Device Development." First International Workshop on the Application of HIFU in Medicine. (May 10/13): 4pp.

Watkin, Kenneth L., PhD; McDonald, Michael A., BS. "Multi/Modal Contrast Agents: A First Step[1]." *Acad Radiol* 2002, 9(suppl 2):S285/S287.

Watkin, Kenneth L., PhD; McDonald, Michael A., BS. "Schematic of the Tube, Cross Section Ultrasound Images of the Tube With Different Contrast Media (CM)." *Acad Radiol* 2002, 9(suppl 2):S288/S289.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non/Gaseous Nanoparticle Contrast Agent[1]," *Acad Radiol* 2002, 9(suppl 2):S290/S293.

Hatangadi, Ram Bansidhar. "A Novel Dual Axis Multiplanar Transesophageal Ultrasound Probe for Three-Dimensional Echocardiograph." *University of Washington, Department of Sciences and Engineering*. (1994), Abstract. vol. 55-11B; 4960pp.

Accord, Ray E. "The Issue of Transmurality in Surgical Ablation for Atrial Fibrillation," Cardiothoracic Surgery Netwowk, Aug. 8, 2005.

Anand, Ajay et al. "Using the ATL 1000 to Collect Domodulated RF Data for Monitoring HIFU Lesion Formation." Center for Industrial and Medical Ultrsound, University of Washington. Abstract. 11pp.

Yu, T., Wang, G., Hu, K., Ma, P., Bai, J., and Wang, Z. "A microbubble agent improves the therapeutic efficiency of high intensity focused ultrasound: A rabbit kidney study." (Abstract) NDN 234-0481-1539-3. *Urol Res*. Feb. 2004; 32(1): 14-9. Epub Dec. 4, 2003.

Amenta et al., "A New Voronoi-Based Surface Reconstruction Algorithm." *Computer Graphics*; 7pp. 1998.

American Red Cross., "Blood 101." 4pp., Dec. 11, 2007.

Anand et al., "Monitoring formation of high intensity focused ultrasound (HIFU) induced lesions using backscattered ultrasound." *Acoustical Society of America*; Mar. 10, 2004.

(56) References Cited

OTHER PUBLICATIONS

Aurenhammer, F., "Voronoi diagrams—A Survey of Fundamental Geometric Data Structure." *ACM Computing Surveys*, vol. 23, No. 3: 345-405, Sep. 1991.
Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.
Beard et al., "An Annular Focus Ultrasonic Lens for Local Hyperthermia Treatment of Small Tumors." *Ultrasound in Medicine & Biology*; vol. 8, No. 2: 177-184, 1982.
Bokarewa et al., "Tissue factor as a proinflammatory agent." *Arthritis Research*, vol. 4: 190-195, Jan. 10, 2002.
Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.
Buller et al., "Accurate Three-dimensional Wall Thickness Measurement From Multi-Slice Short-Axis MR Imaging." *Computers in Cardiology*, 245-248, 1995.
Chao et al., "Aspheric lens design." *Ultrasonics Symposium, 2000 IEEE*, vol. 2: Abstract Only, Oct. 2000.
Cheliue et al., "Fabrication of Medical Models From Scan Data via Rapid Prototyping Techniques." 9 pp., Feb. 7, 2007.
Chong et al., "Tissue Factor and Thrombin Mediate Myocardial Ischemia- Reperfusion Injury." *The Society of Thoracic Surgeons*, vol. 75: S649-655, 2003.
Dempsey et al., "Thickness of Carotid Artery Atherosclerotic Plaque and Ischemic Risk." *Neurosurgery*, vol. 27, No. 3: 343-348, 1990.
Ebbini et al., "Image-guided noninvasive surgery with ultrasound phased arrays." *SPIE*, vol. 3249: 230-239, Apr. 2, 1998.
Edelsbrunner, Herbert. "Geometry and Topology for Mesh Generation." *Cambridge University Press*: 68pp, 2001.
Ewert et al., "Anti-myeloperoxidase antibodies stimulate neutrophils to damage human endothelial cells." *Kidney International*, vol. 41: 375-383, 1992.
Ganapathy et al., "A New General Triangulation Method for Planar Contours." *Computer Graphics* vol. 16, No. 3:69-75, 1982.
Gray, Henry. "The Skull." *Anatomy of the Human Body*: 7pp., 1918.
Hadimioglu et al., "High-Efficiency Fresnel Acoustic Lenses." *Ultrasonics Symposium 1993 IEEE*: 579-582, 1993.
Han et al., "A Fast Minimal Path Active Contour Model." IEEE Transactions on Image Processing, vol. 10, No. 6: 865-873, Jun. 2001.
Hubka et al., "Three-dimensional echocardiographic measurement of left ventricular wall thickness: In vitro and in vivo validation." *Journal of the American Society of Echocardiography*, vol. 15, No. 2: 129-135, 2002.
Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.
Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.
Idell et al., "Fibrin Turnover in Lung Inflammation and Neoplasia." *American Journal of Respiratory and Critical Care Medicine*, vol. 163: 578-584, 2001.
Kang et al., "Analysis of the Measurement Precision of Arterial Lumen and Wall Areas Using High-Resolution MRI." *Magnetic Resonance in Medicine*, vol. 44: 968-972, 2000.
Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.
Meyers, D. "Multiresolution tiling." *Computer Graphics*, No. 5: 325-340, 1994.
Miller et al., "Diagnostic ultrasound activation of contrast agent gas bodies induces capillary rupture in mice." *PNAS*, vol. 97, No. 18: 10179-10184, 2000.
O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.
Pignoli et al., "Intimal plus medial thickness of the arterial wall: A direct measurement with ultrasound imaging." *Circulation*, vol. 74, No. 6:1399-1406, Dec. 1986.
Rosen et al., "Vascular Occlusive Diseases." 37pp., revised 2002.
Schulte-Altedorneburg et al., "Accuracy of In Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.
Vaezy et al., "Hemostasis using high intensity focused ultrasound." *European Journal of Ultrasound*, vol. 9: 79-87, 1999.
Vaezy et al., "Intra-operative acoustic hemostasis of liver: production of a homogenate for effective treatment." *Ultrasonics*, vol. 43: 265-269, 2005.
Von Land et al., "Development of an Improved Centerline Wall Motion Model." *IEEE*: 687-690, 1991.
Williamson et al., "Color Doppler Ultrasound Imaging of the Eye and Orbit." *Survey of Ophthamology*, vol. 40, No. 4: 255-267, 1996.
n.a., "Cavitation." Ultrasound TIP—U.S. Database: Dec. 12, 2007.
Aaslid et al., "Noninvasive transcranial Doppler ultrasound recording of flow velocity in basal cerebral arteries." *Journal of Neurosurgery*, vol. 57: 769-774, 1982.
Campbell et al. "Pulsatile Echo-encephalography." *Acta Neurologica Scandinavica Supplementum 45*, vol. 46: 1-57, 1970.
Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.
Gao et al., "Imaging of the Elastic Properties of Tissue—A Review." *Ultrasound in Medicine & Biology*, vol. 22, No. 8: 959-977, 1996.
Klingelhöfer et al., "Chapter 4: Functional Ultrasonographic Imaging" In Babikian VL, Wechsler LR, eds. *Transcranial Doppler Ultrasonography*. Woburn, MA: Butterworth-Heinemann, 49-66, 1999.
Markwalder et al., "Dependency of Blood Flow Velocity in the Middle Cerebral Artery on End-Tidal Carbon Dioxide Partial Pressure—A Transcranial Ultrasound Doppler Study." Journal of Cerebral Blood Flow and Metabolism, vol. 4, No. 3: 368-372, 1984.

\* cited by examiner

| Transducer Frequency, Port Locations† | Electrical Power (W) | Power Lost as Heat (W) | Avg. Rate of Heat Removal (W)‡ | Efficiency with respect to total electrical power** |
|---|---|---|---|---|
| 3.5 MHz, Opposite | 30 | 6.1 | 15.1 | 50.3 |
| 3.5 MHz, Opposite | 50 | 10.1 | 24.3 | 48.6 |
| 3.5 MHz, Opposite | 70 | 14.1 | 33.6 | 48.0 |
| 3.5 MHz, Adjacent | 30 | 6.1 | 14.9 | 49.7 |
| 3.5 MHz, Adjacent | 50 | 10.1 | 16.4 | 32.8 |
| 3.5 MHz, Adjacent | 70 | 14.1 | 24.9 | 35.6 |
| 5.0 MHz, Opposite | 30 | 15.6 | 17.8 | 59.3 |
| 5.0 MHz, Opposite | 50 | 26.0 | 33.3 | 66.6 |
| 5.0 MHz, Opposite | 70 | 36.3 | 48.9 | 69.9 |
| 5.0 MHz, Adjacent | 30 | 15.6 | 16.2 | 54.0 |
| 5.0 MHz, Adjacent | 50 | 26.0 | 30.5 | 61.0 |
| 5.0 MHz, Adjacent | 70 | 36.3 | 46.1 | 65.9 |

*FIG. 6*

ACOUSTIC COUPLER USING AN INDEPENDENT WATER PILLOW WITH CIRCULATION FOR COOLING A TRANSDUCER

RELATED APPLICATIONS

This application is based on a prior copending provisional application, Ser. No. 60/610,451, filed on Sep. 16, 2004, the benefit of the filing date of which is hereby claimed under 35 U.S.C. §119(e). The present application is further a continuation-in-part application of patent application Ser. No. 10/977,339, filed Oct. 29, 2004, the benefit of the filing date of which are hereby claimed under 35 U.S.C. §120.

GOVERNMENT RIGHTS

This invention was made with U.S. Government support under grant No. 2-R42-HD38440-02 awarded by the National Institutes of Health, and grant Nos. N00014-01-96-0630 and N00014-01-G-0460, awarded by the Department of the Navy. The U.S. Government has certain rights in the invention.

BACKGROUND

Ultrasound is widely used for imaging a patient's internal structures without risk of exposure to potentially harmful radiation, as may occur when using X-rays for imaging. An ultrasound examination is a safe diagnostic procedure that uses high frequency sound waves to produce an image of the internal structures of a patient's body. Many studies have shown that these sound waves are harmless and may be used with complete safety, even to visualize the fetus in pregnant women, where the use of X-rays would be inappropriate. Furthermore, ultrasound examinations generally require less time than examinations using other imaging techniques, and ultrasound examinations are typically less expensive than examinations using other imaging techniques.

More recently, the use of high intensity focused ultrasound (HIFU) for therapeutic purposes, as opposed to imaging, has received significant attention in the medical community. HIFU therapy employs ultrasound transducers that are capable of delivering 1,000-10,000 W/cm$^2$ to a focal spot, in contrast to diagnostic imaging ultrasound, where intensity levels are usually below 0.1 W/cm$^2$. A portion of the energy from these high intensity sound waves is transferred to a targeted location as thermal energy. The amount of thermal energy thus transferred can be sufficiently intense to cauterize undesired tissue, or to cause necrosis of undesired tissue (by inducing a temperature rise greater than about 70° C.) without actual physical charring of the tissue. Tissue necrosis can also be achieved by mechanical action alone (i.e., by cavitation that results in mechanical disruption of the tissue structure). Further, where the vascular system supplying blood to an internal structure is targeted, HIFU can be used to induce hemostasis. The focal region of this energy transfer can be tightly controlled so as to obtain necrosis of abnormal or undesired tissue in a small target area without damaging adjoining normal tissue. Thus, deep-seated tumors can be destroyed with HIFU without surgical exposure of the tumor site.

An important component in any type of ultrasound therapy system is the mechanism for coupling the acoustic energy into the tissue. Good acoustic coupler is necessary to efficiently transfer the ultrasound energy from the transducer to the treatment site. The ideal acoustic coupler is a homogenous medium that has low attenuation, and an acoustic impedance similar to that of the tissue being treated. Due to its desirable acoustic transmission characteristics, water has commonly been used as the coupling medium in many therapeutic applications of ultrasound.

In previous hemostasis studies in which HIFU has been used to arrest bleeding of injured blood vessels and organs, the HIFU transducer was contained within a water-filled, conical, plastic housing with a thin, polyurethane membrane at the tip. This coupler was designed for superficial treatments, since it places the HIFU focus only several millimeters beyond the tip of the water-filled cone. While this coupling method has been useful for hemostasis experiments, it has many drawbacks that would make it impractical for a clinical setting. These disadvantages include requirements for degassing, sterilization, and circulation and containment issues. Due to the limitations of the current HIFU applicators, an alternative coupling medium is desirable.

Latex condoms have been used as a disposable sheath for rectal and vaginal ultrasound probes, and when filled with water, such sheaths facilitate acoustic coupling. With respect to HIFU therapy probes, a HIFU transducer can generate significant amounts of heat, which should be dissipated to protect the patient and to prolong the life of the transducer. Latex condoms, and ultrasound probe sheaths specifically intended for such ultrasound coupling, are not designed to facilitate circulation of a cooling liquid.

It would be desirable to provide a disposable acoustic coupler for use with ultrasound probes, configured to circulate a cooling liquid proximate an ultrasound transducer.

SUMMARY

Disclosed herein is an acoustic coupler that facilitates acoustically coupling an acoustic device (such as an ultrasound imaging transducer or an ultrasound therapy transducer) to a physical mass, where the acoustic device is configured to direct acoustic energy into or through the physical mass. The physical mass is generally biological tissue, although no limitation is implied with respect to the type of physical mass to which the acoustic energy is directed. The acoustic coupler includes a liquid chamber (e.g., a water pillow) having a first surface configured to conform to a transducer, and a second surface configured to conform to the physical mass into which the acoustic energy provided by the transducer is to be directed. The liquid chamber further includes a liquid inlet configured to be coupled to a liquid supply, and a liquid outlet configured to be coupled to a discharge volume. A pump can be used to circulate liquid through the liquid chamber to dissipate heat generated by the transducer. Generally, the liquid chamber is filled with water (or saline solution), although the use of water in this embodiment should not be considered to be a limitation on the concept.

Preferably, the first surface (configured to conform to the transducer) provides cooling to the front face of the transducer. The acoustic coupler further preferably exhibits one or more of the following characteristics: the acoustic coupler is formed from biocompatible materials, the acoustic coupler exhibits a low attenuation, a liquid pressure in the liquid chamber of the acoustic coupler can be varied to achieve various standoffs, the acoustic coupler is formed from materials that can be sterilized, and the acoustic coupler device can be viewed as disposable.

In one implementation, the acoustic coupler includes a pouch coupled to the liquid chamber. The pouch defines an open-ended volume configured to receive a transducer, so that the pouch can be used to attach the acoustic coupler to the transducer. Preferably, the pouch is formed from a flexible and elastomeric material, such that the acoustic coupler is attached to the transducer via an interference fit. The dimensions of the pouch can be varied to accommodate specific transducer configurations. In some embodiments, the pouch is configured to encompass the transducer and at least a portion of a handle or probe supporting the transducer.

The liquid inlet and liquid outlet of the liquid chamber are preferably configured to enhance a circulation of liquid in the liquid chamber. Various different configurations can be empirically tested to determine the effectiveness of a specific configuration. Exemplary configurations include disposing the liquid inlet substantially adjacent to the liquid outlet, as well as disposing the liquid inlet substantially opposed to the liquid outlet. In some embodiments, the liquid inlet and liquid outlet are separated by an acute angle. In some embodiments, the liquid inlet and liquid outlet are separated by an angle of between about 40° and about 100°.

At least one of the first surface (configured to conform to the front face of the transducer), and the second surface (configured to conform to the physical mass) can include at least one opening to allow liquid from the liquid chamber to wet the surface, thereby enhancing the acoustic coupler between the surface and the transducer and/or the physical mass. Preferably, a surface configured to "weep" liquid to facilitate coupling will include a plurality of small pores that release sufficient liquid to facilitate coupling, without releasing excessive amounts of liquid. Various different agents can be added to the liquid used to inflate the liquid chamber, to be released through such pores. Such agents can include ultrasound contrast agents, therapeutic agents, and sterilization agents.

A system configured to be used with such acoustic couplers preferably includes a liquid supply, a pump configured to circulate the liquid, and a cooling unit configured to thermally condition the liquid. A degassing unit, such as a second pump, is preferably included to remove gas bubbles from the liquid. In some embodiments, a liquid line coupling the liquid supply to the liquid inlet is larger than a liquid line coupling the liquid outlet to the liquid supply, to increase a flow resistance on the outlet of the liquid chamber relative to its inlet.

A related method for acoustically coupling a transducer to a physical mass while providing cooling to the transducer includes the steps of positioning a liquid chamber between the physical mass and the transducer, introducing a liquid into the liquid chamber, such that a first surface of the liquid chamber conforms to the transducer and a second surface of the liquid chamber conforms to the physical mass, and introducing additional liquid into the liquid chamber, thereby establishing a circulating flow of liquid that absorbs heat from the transducer, providing cooling to the transducer. Additional method steps relate to releasing a portion of liquid disposed within the liquid chamber from at least one of the first surface and the second surface to facilitate acoustically coupling the surface to the transducer and/or physical mass. Yet another method step relates to securing the liquid chamber to the transducer using a pouch defining an open-ended volume configured to achieve a snug fit with the transducer.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A schematically illustrates a first embodiment of an acoustic coupler including a liquid chamber configured to acoustically couple a transducer to a physical mass, and to circulate a cooling liquid to cool the transducer, as well as a pouch configured to attach the acoustic coupler to the transducer;

FIG. 1B schematically illustrates an exemplary acoustic device including a transducer and a handle;

FIG. 1C schematically illustrates an acoustic coupler in FIG. 1A that is attached to an acoustic device of FIG. 1B;

FIG. 1D is an enlarged view of the liquid chamber portion of the acoustic coupler of FIG. 1A, illustrating that the liquid chamber includes a first surface configured to conform to the transducer, and a second surface configured to conform to a physical mass into which acoustic energy from the transducer is to be directed;

FIG. 2A schematically illustrates a second embodiment of an acoustic coupler configured to be attached to a different type of acoustic device;

FIG. 2B schematically illustrates another exemplary acoustic device including a transducer and a handle;

FIG. 2C schematically illustrates the acoustic coupler of FIG. 2A attached to the exemplary acoustic device of FIG. 2B;

FIGS. 2D and 2E are views of the liquid chamber portion of the acoustic coupler of FIG. 2A, illustrating that an opening or pores can be provided in a wall of the liquid chamber to enable liquid from the liquid chamber to be released, to enhance an acoustic coupler between the liquid chamber and at least one of the transducer and the physical mass;

FIG. 2F schematically illustrates an alternative configuration for a liquid inlet and a liquid outlet portion of the liquid chamber of FIG. 2A, wherein an angle of about 100° is defined between the liquid inlet and liquid outlet;

FIG. 2G schematically illustrates an alternative configuration for a liquid inlet and a liquid outlet portion of the liquid chamber of FIG. 2A, wherein an angle of about 40° is defined between the liquid inlet and liquid outlet;

Figure 4A:
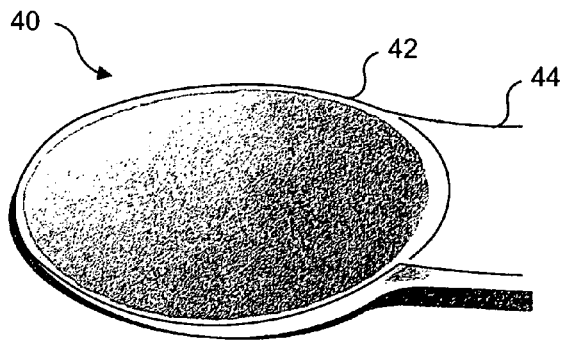
Figure 4B:
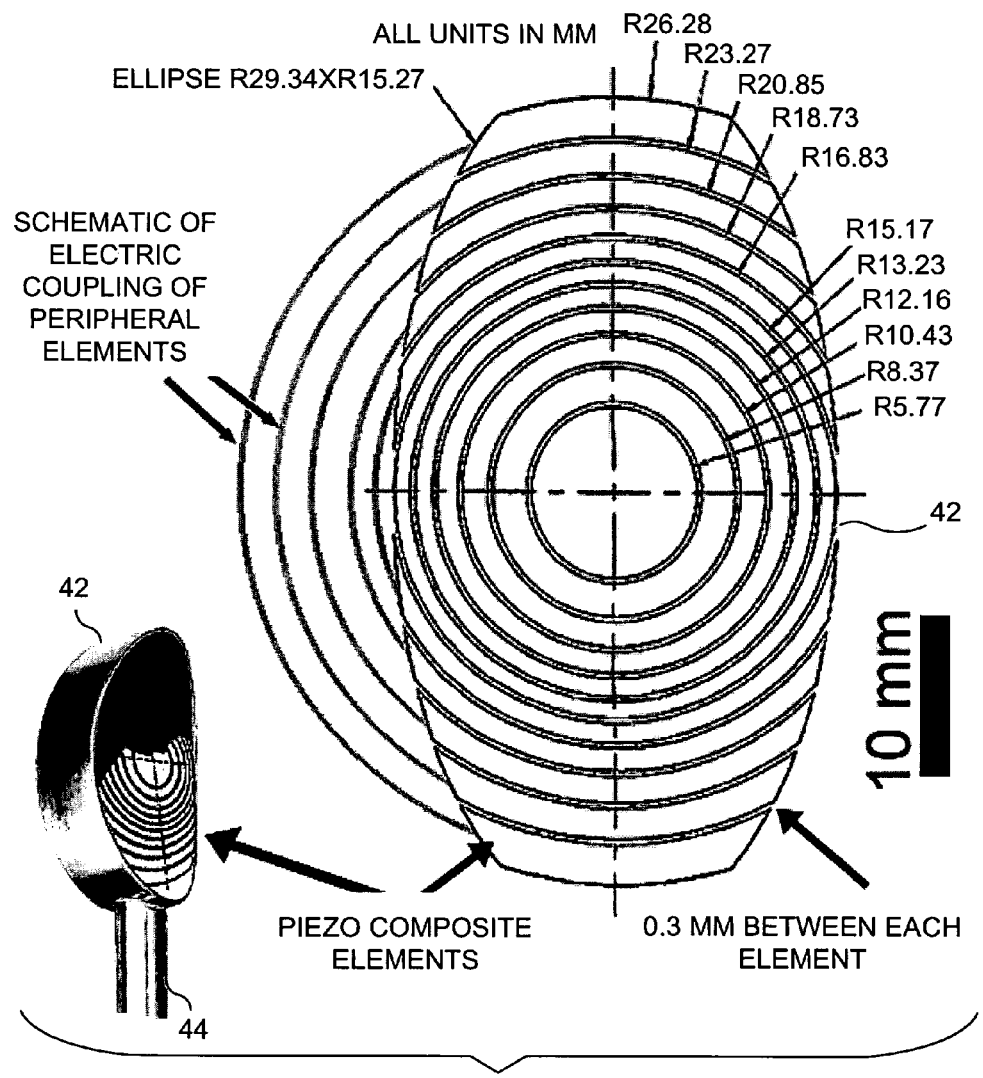
Figure 4C:
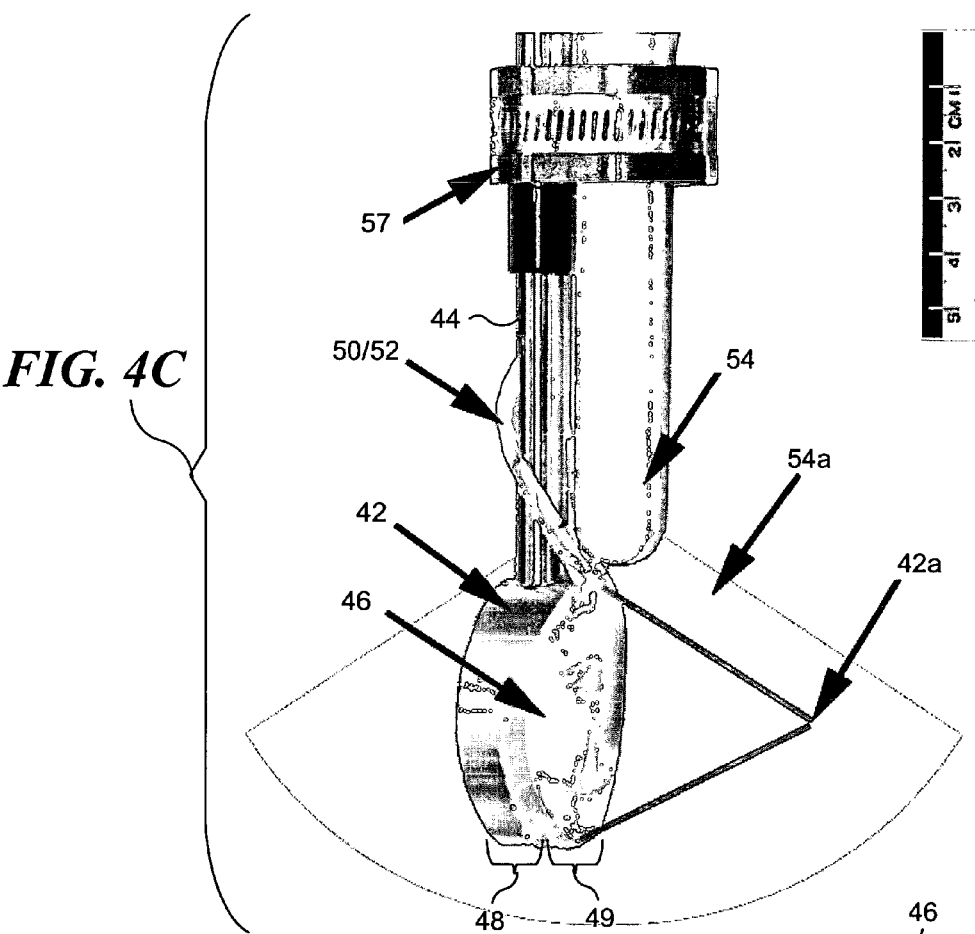
Figure 4D:
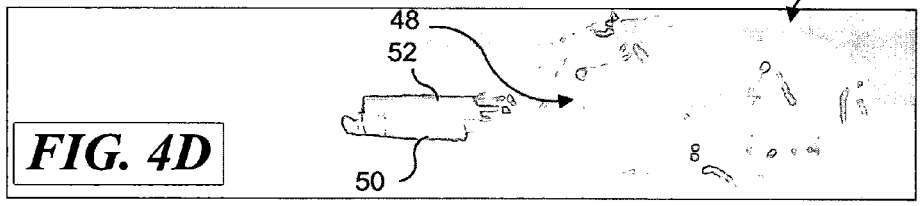
Figure 4E:
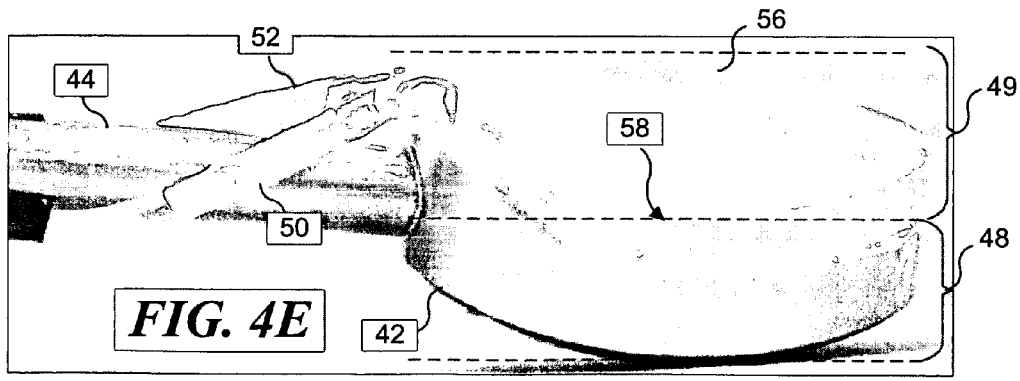
Figures 5A, 5B:
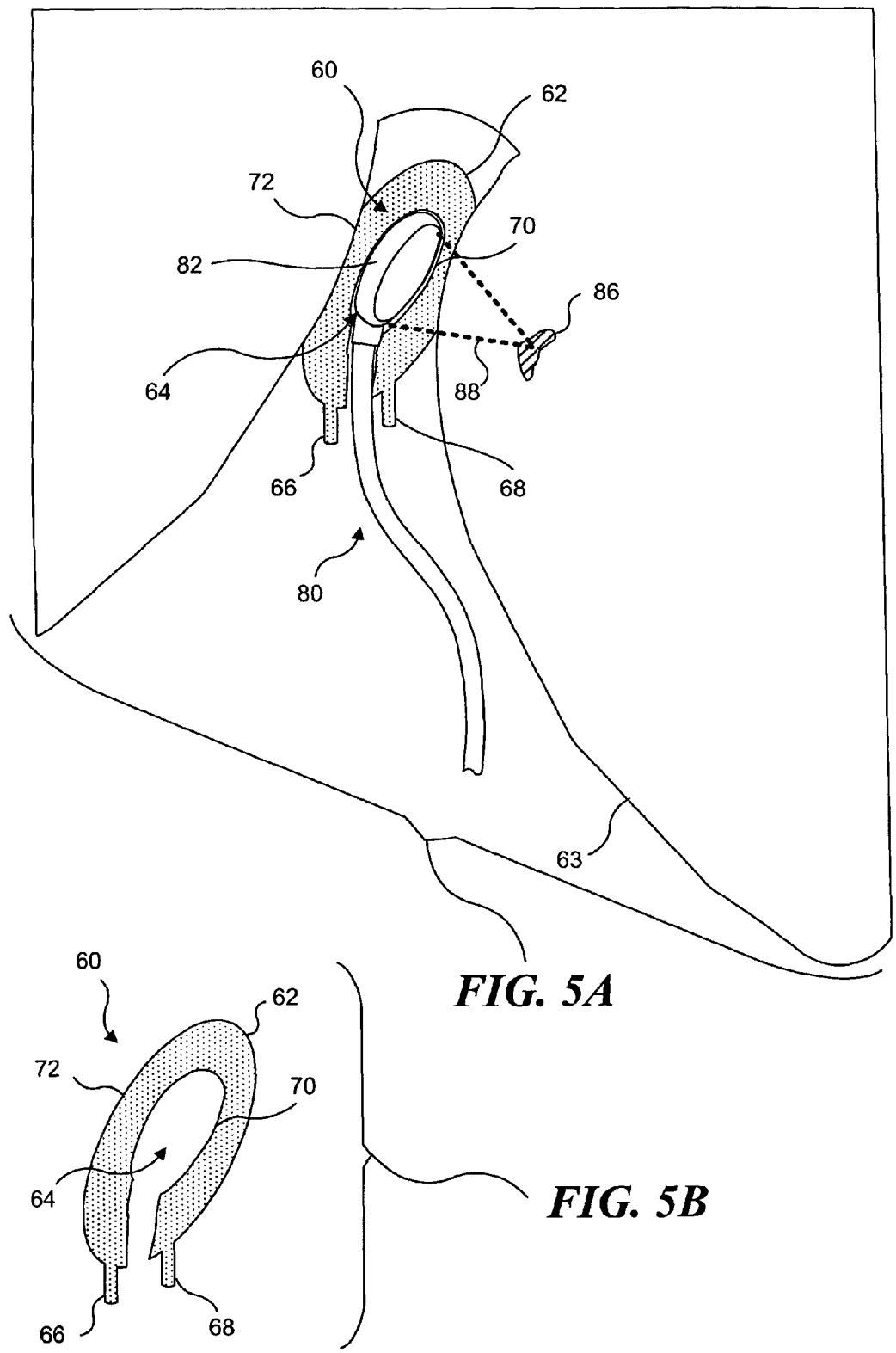
Figure 7:
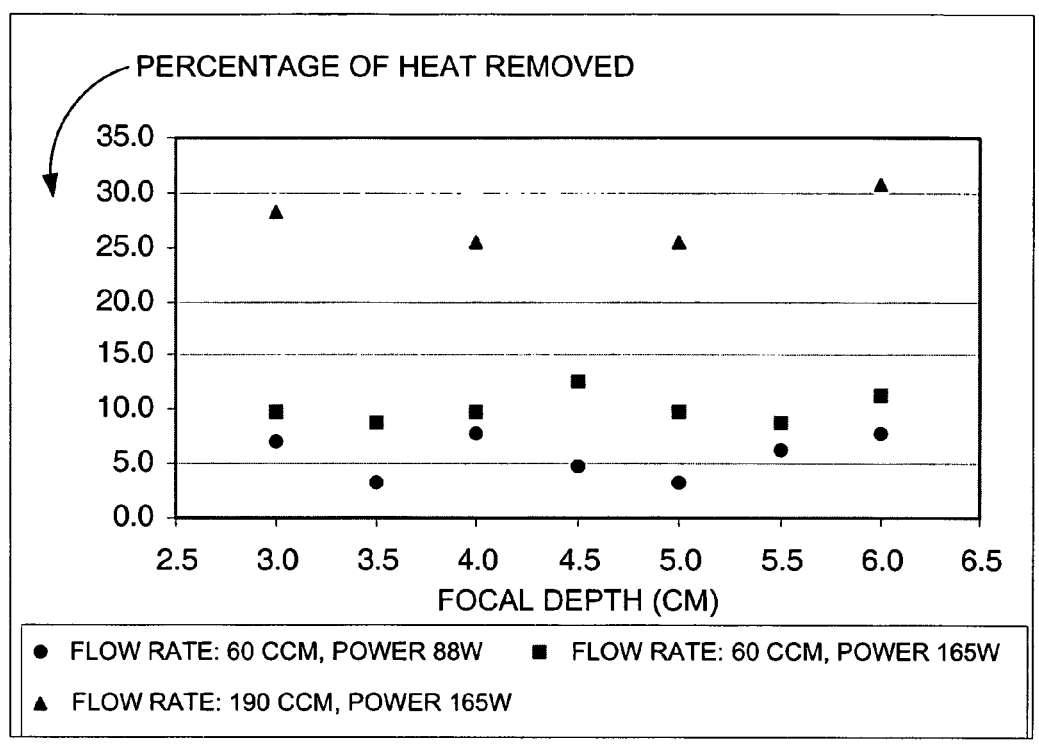

FIG. 4A schematically illustrates another exemplary acoustic device, including a generally spoon shaped transducer, and a handle;

FIG. 4B illustrates additional details for the structure of the acoustic device of FIG. 4A;

FIG. 4C is an image of the acoustic device of FIG. 4A and yet another embodiment of an acoustic coupler;

FIG. 4D is an image of the acoustic coupler configured to be used with the acoustic device of FIG. 4A;

FIG. 4E is an image of the acoustic coupler of FIG. 4D attached to the acoustic device of FIG. 4A;

FIG. 5A schematically illustrates yet another embodiment of an acoustic coupler being used to acoustically couple the transducer of an acoustic device to tissue;

FIG. 5B is an enlarged view of the acoustic coupler of FIG. 5A, illustrating that the pouch portion of the acoustic coupler is disposed in a central portion of the acoustic coupler, such that when the acoustic coupler is attached to an acoustic device, the acoustic coupler substantially encompasses the acoustic device, proximate to the transducer;

FIG. 6 is a chart illustrating that exemplary acoustic couplers as described herein can achieve satisfactory cooling of a HIFU transducer; and FIG. 7 graphically illustrates the percentage of heat removed by an acoustic coupler including a liquid chamber, as a function of a focal depth of the transducer.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

Figure 1A:
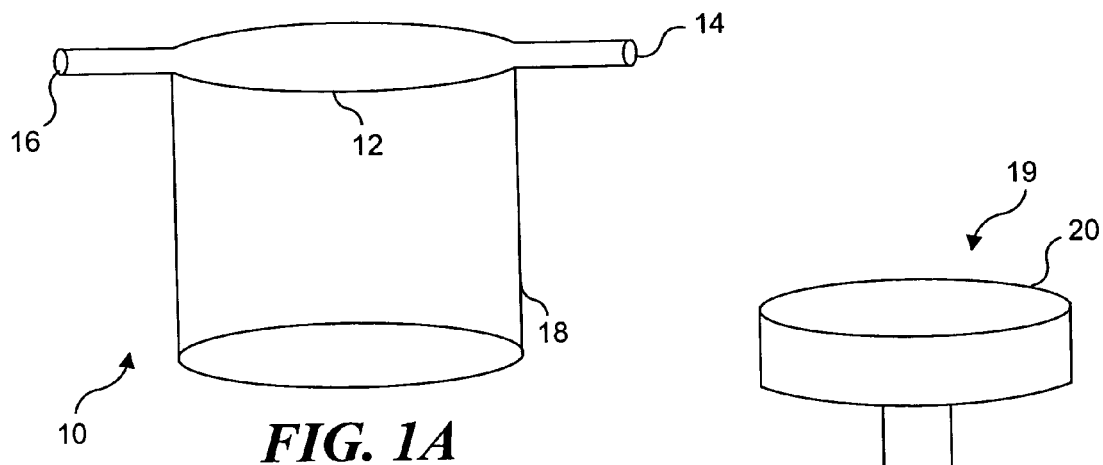

FIG. 1A schematically illustrates a first embodiment of an acoustic coupler 10 including a liquid chamber 12 configured to acoustically couple a transducer to a physical mass and to circulate a cooling liquid to cool the transducer, as well as a pouch 18 configured to attach the acoustic coupler to the transducer. Liquid chamber 12 includes a liquid inlet 14 and a liquid outlet 16. Liquid, such as water or a saline solution, can be introduced into liquid chamber 12 via liquid inlet 14. Note that pouch 18 defines an open-ended volume that is sized and shaped to accommodate a transducer. Preferably, pouch 18 is formed from a flexible (elastomeric) material so that acoustic coupler 10 can be attached to a transducer (or an acoustic device including a transducer) by an interference fit between the acoustic coupler and the device.

Figure 1B:
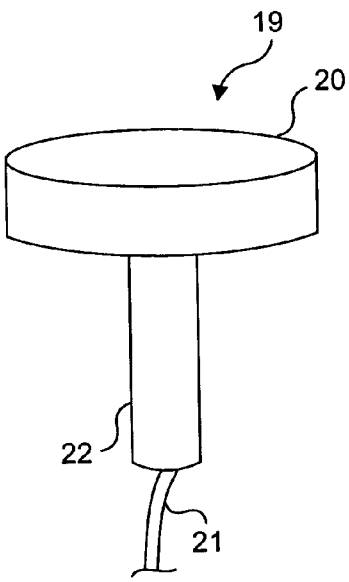

FIG. 1B schematically illustrates an exemplary acoustic device 19 including a transducer 20, a handle 22, and a lead 21 that couples the transducer to a power supply (not shown). In general, transducer 20 will be a HIFU therapy transducer configured to emit ultrasound waves sufficiently energetic to induce a therapeutic effect at a treatment site. The terms "therapeutic transducer," "HIFU transducer," and "high intensity transducer," as used herein, all refer to a transducer that is capable of being energized to produce ultrasonic waves that are much more energetic than the ultrasonic pulses produced by an imaging transducer and which can be focused or directed onto a discrete location, such as a treatment site in a target area. Such transducers generally generate more heat during use than ultrasound imaging transducers. Thus, HIFU transducers have a greater need for cooling than do imaging transducers. However, while the acoustic couplers disclosed herein are expected to be particularly beneficial when used with a HIFU transducer, it should be recognized that these acoustic couplers are not limited for use in connection with any specific transducer. Furthermore, it should be recognized that the acoustic couplers disclosed herein can be configured to be used with many different shapes of transducers, and with many different acoustic devices incorporating transducers.

Figure 1C:
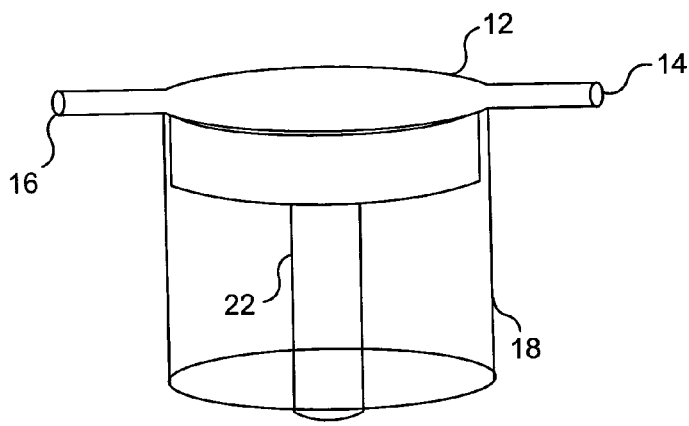
Figure 1D:
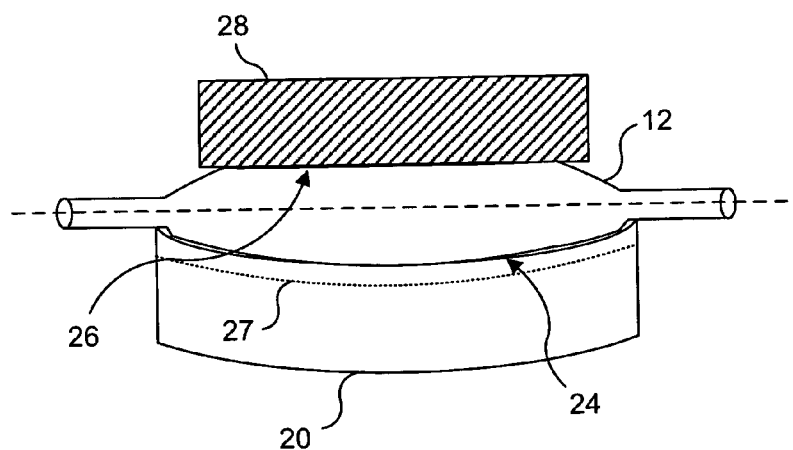

FIG. 1C schematically illustrates acoustic coupler 10 of FIG. 1A attached to acoustic device 19 of FIG. 1B. Note that transducer 20 is encompassed by the open-ended volume of pouch 18. As illustrated in FIG. 1D, when acoustic coupler 10 is properly positioned relative to acoustic device 19, and liquid chamber 12 is filled with a liquid, a surface 24 of liquid chamber 12 substantially conforms to transducer 20. It should be recognized that there exists significant variation in acoustic devices incorporating transducers. For example, in some acoustic devices (particularly devices configured for HIFU therapy), a front face of the transducer is exposed. When acoustic coupler 10 is used with an acoustic device including a transducer whose front face is exposed, surface 24 will generally conform to the front face of the transducer. Some acoustic devices include a transducer to which an optional lens 20a (see FIG. 1D) has been attached. For example, aluminum lenses are sometimes employed to achieve better focusing of a HIFU transducer. When acoustic coupler 10 is used with an acoustic device including a transducer to which such a lens has been coupled, surface 24 will generally conform to the front face of the lens. Because such lenses normally exhibit good heat transfer properties, cooling the lens will also cool the underlying transducer. Furthermore, some acoustic devices incorporate a relatively thin housing to enclose a transducer. When acoustic coupler 10 is used with an acoustic device in which the transducer is covered by such a housing, surface 24 will generally conform to the housing, covering the transducer. Again, such housings are generally formed from a relatively thin material, so that cooling the housing proximate the transducer will also cool the underlying transducer. Therefore, it should be recognized that in respect to the following disclosure and the claims that follow, where terms such as "substantially conforms to a transducer," "substantially conforms to the transducer," "conforms to a transducer," and "conforms to the transducer" are employed, such language is intended to encompass the ability of the acoustic coupler to conform to a lens that is coupled to the transducer, as well as conforming to a housing encapsulating the transducer.

Referring once again to FIG. 1D, liquid chamber 12 further includes a surface 26 configured to conform to a physical mass 28 into which acoustic energy from the transducer is to be directed. Either or both surfaces 24 and surface 26 can be coated with mineral oil (or some other coupling medium or coupling gel) to ensure adequate acoustic coupling is achieved.

As noted above, the acoustic couplers disclosed herein preferably exhibit one or more of the following characteristics: biocompatibility, low attenuation, variability of liquid pressure in the liquid chamber enabling different standoffs to be achieved, sterilizability, and disposability. The acoustic couplers disclosed herein can be formed of a polymer material, such as polyurethane. Such a material is biocompatible, sterilizable, has a low attenuation, is flexible (so that the material readily conforms to a physical mass as well as to a transducer, or lens or housing as noted above), and is able to achieve an interference fit with an acoustic device (where dimensions of the pouch have been selected to accommodate a particular form factor for an acoustic device). In some embodiments, the pouch is oversized, so that a wider variation of form factors can be accommodated. In such embodiments, additional attachment mechanisms can be employed, such as straps, couplings, or elastic bands, to secure the acoustic coupler to the acoustic device.

Figure 2A:
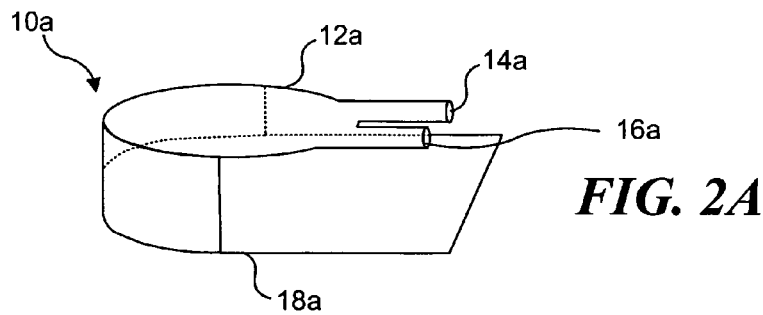
FIG. 2H is an image of the acoustic coupler of FIG. 2A attached to the acoustic device of FIG. 2B, illustrating how a liquid pressure in the liquid chamber can be varied to achieve a different standoff.

FIG. 2A schematically illustrates a second embodiment of an acoustic coupler configured to be attached to a different type of acoustic device. Acoustic coupler 10a includes a liquid chamber 12a, a liquid inlet 14a, a liquid outlet 16a, and a pouch 18a. Once again, pouch 18a defines an open-ended volume configured to receive a transducer. Note that the size and shape of pouch 18a of FIG. 2A is different than the size and shape of pouch 18 in FIG. 1A, because acoustic coupler 10a (FIG. 2A) is configured to be used with a different acoustic device than is acoustic coupler 10 (FIG. 1A).

Figure 2B:
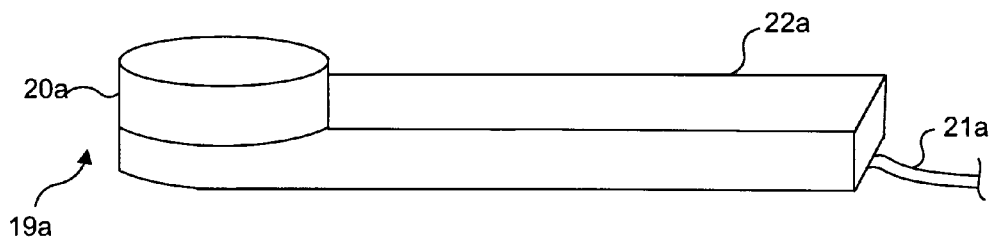

FIG. 2B schematically illustrates an exemplary acoustic device 19a including a transducer 20a, a handle 22a, and a lead 21a that couples the transducer to a power supply (not shown). Once again, transducer 20a will likely be a HIFU therapy transducer, although this exemplary use of the acoustic couplers with HIFU transducers is not intended to represent a limitation.

Figure 2C:
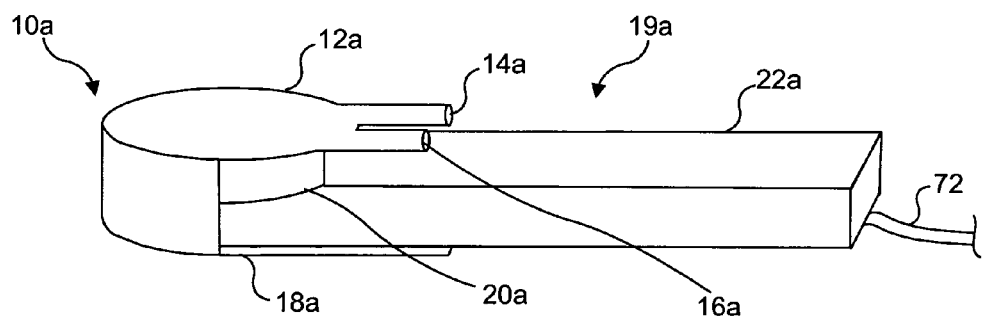
Figure 2D:
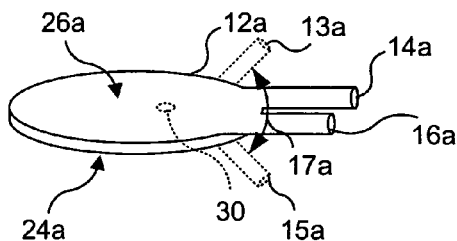

FIG. 2C schematically illustrates acoustic coupler 10a of FIG. 2A attached to acoustic device 19a of FIG. 2B. Note that transducer 20a is substantially encompassed by the open-ended volume of pouch 18a. As illustrated in FIG. 2D, acoustic coupler 10a includes a surface 24a configured to conform to a transducer (or to a lens attached to a transducer, or to a housing enclosing a transducer, generally as described above). Acoustic coupler 10a further includes a surface 26a configured to conform to a physical mass (not shown) into which acoustic energy from the transducer is to be directed. It should be noted that pouch 18a not only encompasses transducer 20a, but also a portion of handle 22a supporting transducer 20a. Preferably, pouch 18a has dimensions selected to accommodate the form factor of acoustic device 19a, so that an interference fit is achieved when transducer 20a and the portion of handle 22a supporting transducer 20a are introduced into pouch 18a. As noted above, some embodiments will incorporate an oversized pouch, to accommodate a wider range of acoustic device form factors, and then use other attachments to secure the acoustic coupler to the acoustic device.

Figure 2E:
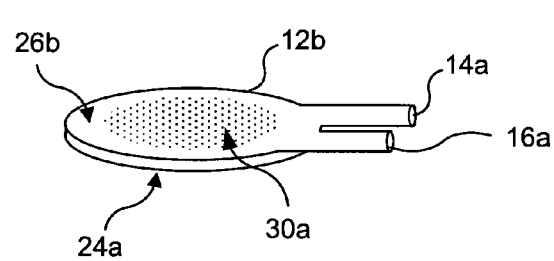

Referring once again to FIG. 2D, surface 26a can optionally include a least one opening configured to enable a liquid in liquid chamber 12a to wet surface 26a, thereby enhancing the acoustic coupler between surface 26a and the physical mass. While not specifically shown, it should be recognized that such openings can also be beneficially incorporated into surface 24a, to similarly enhance the acoustic coupler between surface 24a and the transducer (or a lens covering the transducer, or a housing covering the transducer, generally as described above). Preferably, the size, shape, and location of such openings are selected to generate a thin layer of liquid on the surface without releasing substantially more liquid than is required to facilitate coupling. In some specific applications, it may be desirable to continually flush the physical mass to which the acoustic device is being coupled with a liquid. (For example, an acoustic device configured to provide emergency treatment in field conditions may incorporate openings providing sufficient liquid flow to continually flush the physical mass.) In such embodiments, the openings will be sized, shaped, and oriented to achieve the desired flow. FIG. 2E schematically illustrates a liquid chamber 12b, which includes a plurality of pores (generally indicated by an arrow 30a) configured to wet a surface 26b with liquid flowing from liquid chamber 12b. Particularly in embodiments where the wall or surface of the liquid chamber configured to couple with the physical mass toward which the acoustic device is directing acoustic energy includes at least one opening, that opening can be used to deliver a plurality of different agents to the surface. Such agents can include ultrasound contrast agents, therapeutic agents, and sterilization agents. Particularly with respect to the acoustic device configured to provide emergency treatment under field conditions noted above, disinfectant agents can be introduced into the liquid to prevent potential infections.

Figure 2F:
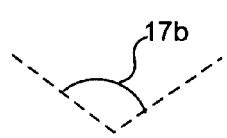
Figure 2G:

Referring once again to acoustic coupler 10 of FIG. 1A, note that liquid inlet 14 and liquid outlet 16 are substantially opposite each other (i.e., an angle of about 180° is defined between them). In contrast, liquid inlet 14a and liquid outlet 16a of acoustic coupler 10a (FIG. 2A) are substantially adjacent (i.e., they are separated by an angle of about 0°). It should be recognized that the relative orientations of the liquid inlet and the liquid outlet can effect a circulation of the liquid within the liquid chamber, which in turn, can affect the ability of the circulating liquid to dissipate heat generated by the transducer. The liquid inlet and liquid outlet of the liquid chamber are preferably configured to enhance a circulation of liquid in the liquid chamber. Various different configurations can be empirically tested to determine the effectiveness of a specific configuration. Exemplary configurations include disposing the liquid inlet substantially adjacent to the liquid outlet (as exemplified by acoustic coupler 10a of FIG. 2A), as well as disposing the liquid inlet substantially opposite to the liquid outlet (as exemplified by acoustic coupler 10 of FIG. 1A). In some embodiments, the liquid inlet and liquid outlet are separated by an acute angle, as is schematically illustrated in FIG. 2D by a liquid inlet 13a and a liquid outlet 15a, where an acute angle 17a separates the liquid inlet from the liquid outlet. In some embodiments, the liquid inlet and liquid outlet are separated by an angle of between about 40° to about 100°. FIG. 2F schematically illustrates an angle 17b of about 100°, while FIG. 2G schematically illustrates an angle 17c of about 40°, either of which can be used as a separation angle between the liquid inlet and the liquid outlet (as well as any angle in between). Empirical studies with acoustic coupler 10 and acoustic coupler 10a have indicated that acoustic couplers having a liquid inlet that is substantially opposite to the liquid outlet exhibit higher heat removal rates. However, the difference between the heat removal rate for acoustic coupler 10 and acoustic coupler 10a was not significant for small, relatively low-power transducers, and only becomes significant when relatively larger transducers, generating more heat, are employed.

Figure 2H:
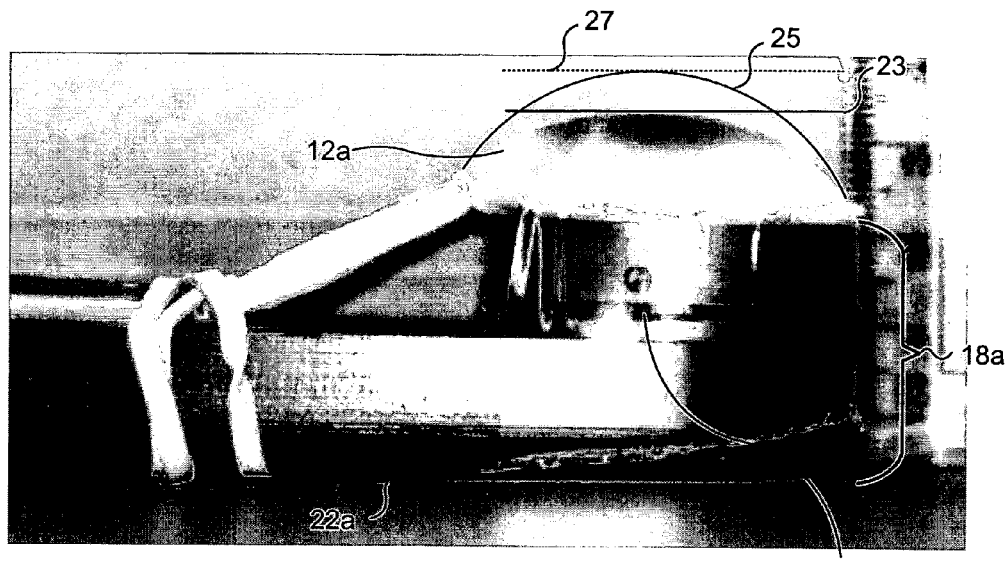

FIG. 2H is an image of acoustic coupler 10a of FIG. 2A attached to acoustic device 19a of FIG. 2B, illustrating how a liquid pressure in liquid chamber 12a can be varied to achieve a different standoff. When a first liquid pressure is used, liquid chamber 12a inflates to a maximum height indicated by a line 23. Increasing the amount of liquid forced into the liquid chamber increases the pressure and causes liquid chamber 12a to inflate further (generally as indicated by a curve 25), so that it exhibits a different maximum height, generally as indicated by a line 27. Variation of the liquid pressure in the liquid chamber can thus be used to achieve different standoffs.

Figure 3:
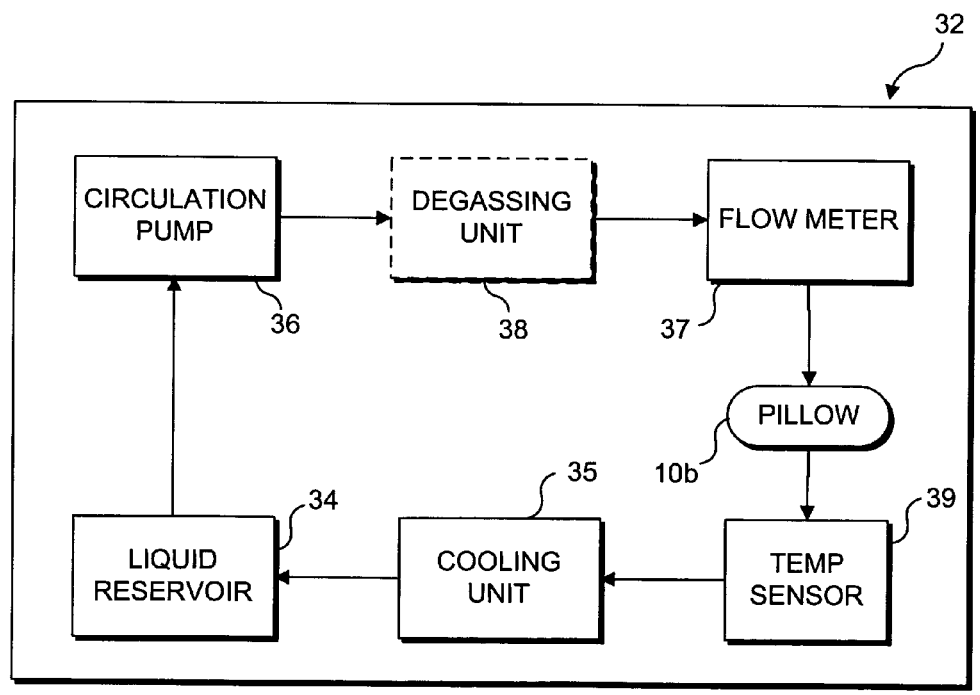
FIG. 3 is a functional block diagram of a system including an acoustic coupler, such as illustrated in FIGS. 1A and 2A, a circulation pump, a liquid reservoir, a cooling unit, a flow meter, and a degassing unit.

FIG. 3 is a functional block diagram of a system 32 including an acoustic coupler 10b (such as illustrated in FIGS. 1A and 2A), a circulation pump 36, a liquid reservoir 34, a cooling unit 35, a flow meter 37, a temperature sensor 39, and an optional (but preferred) degassing unit 38. The function of circulation pump 36 is to provide a motive force for establishing a circulating liquid within the liquid chamber of acoustic coupler 10b. The function of liquid reservoir 34 is to provide a supply of the circulatory liquid, such as water or saline solution, and to receive cooled liquid from cooling unit 35. Note cooling unit 35 can be beneficially implemented using a combination fan and heat exchanger. Those of ordinary skill in the art will recognize that many types of cooling units can be employed, such as thermoelectric coolers and other types of electromechanical chillers.

It should be understood that the relative position of the cooling unit is not important. For example, FIG. 3 indicates that the cooling unit is coupled in fluid communication with the liquid outlet of the acoustic coupler, such that the liquid returning from the acoustic coupler is cooled before being returned to the liquid supply for recirculation. An alternative configuration would be to position the cooling unit between the liquid supply and the liquid inlet of the acoustic coupler, such that the liquid is cooled before it is introduced into the liquid volume, rather than being cooled after it has exited the liquid volume.

Temperature sensor 39 can be disposed in a number of different locations. A temperature sensor can be introduced into the liquid chamber of acoustic coupler 10b, or into one or both of the liquid inlet and liquid outlet of acoustic coupler 10b. The purpose of the temperature sensor is to monitor the temperature of the circulating liquid, to determine if additional cooling or additional chilled liquid flow are required to sufficiently cool the transducer. Flow meter 37 can be implemented using one or more valves configured to enable a flow rate to be varied, and preferably includes a meter providing an indication of a current flow rate, as well as the one or more valves to control it. In an empirical system developed to test the concept disclosed herein, degassing unit 38 was implemented using an additional pump. Those of ordinary skill in the art will recognize that other conventional degassing techniques can be employed. In the empirical system noted above, a flow resistance on the liquid outlet of the acoustic coupler was increased relative to that of the liquid inlet, by providing a larger liquid line coupling the liquid inlet of the acoustic coupler to the liquid supply than was provided to couple the liquid outlet of the acoustic coupler to the cooling unit.

FIG. 4A schematically illustrates another exemplary acoustic device 40, which includes a generally spoon shaped transducer 42 and a handle 44. Transducer 42 is a phased array transducer including 11 different transducer elements, six of which have complete annuli, and five of which have truncated annuli. Transducer 42 exhibits a focal range of about 3-6 cm.

FIG. 4B illustrates additional details of transducer 42, clearly showing the plurality of different emitter elements that are included therein. Generally spoon-shaped transducer 42 includes 11 discrete emitter elements, all equal in area, each element being separated from its neighbors by about 0.3 mm. Six of the emitter elements have complete annuli, and five emitter elements have truncated annuli. The overall transducer dimensions are about 35 mm×60 mm. Generally spoon-shaped transducer 42 has a center frequency of around 3 MHz, a focal length of about 3-6 cm, a geometric focus of about 5 cm, and a maximum focal intensity of about 3000 W/cm$^2$.

FIG. 4C is an image of acoustic device 40 of FIG. 4A, and yet another embodiment of an acoustic coupler. An ultrasound imaging probe 54 is coupled to acoustic device 40 (a HIFU therapy probe) via a mechanical coupling 57, to facilitate simultaneous imaging and therapy. An image plane 54a is provided by imaging probe 54, and acoustic device 40 provides a highly focused acoustic beam 42a. An acoustic coupler 46 has been attached to transducer 42. Acoustic coupler 46 includes a liquid inlet 50, a liquid outlet 52, a liquid chamber 49, and an open-ended pouch 48 (having a size and shape selected to correspond to a size and shape of transducer 42). Acoustic coupler 46 is attached to transducer 42 via an interference fit provided by pouch 48.

In an empirical study, acoustic coupler 46 was fashioned out of polyurethane, and a pump circulated water over the face of transducer 42 at a rate of approximately 60 ml/min. That rate was determined empirically to avoid over-inflation of the liquid chamber, and ensure that the transducer temperature did not rise above 40° C. Water was selected as the cooling medium, due to its ease of handling and its effectiveness as a transducer coolant.

FIG. 4D is an image of acoustic coupler 46 before being attached to transducer 42, more clearly showing liquid inlet 50, liquid outlet 52, and pouch 48. FIG. 4E is an image of acoustic coupler 46 of FIG. 4D attached to acoustic device 40 of FIG. 4A, illustrating that liquid chamber 49 includes a surface 58 configured to conform to transducer 42, and a surface 56 configured to conform to a physical mass into which transducer 42 emits highly focused beam 42a.

FIG. 5A schematically illustrates yet another embodiment of an acoustic coupler being used to acoustically couple a transducer of an acoustic device to tissue. An acoustic device 80, including a therapeutic transducer 82, has been introduced into a body cavity and is positioned such that a highly focused acoustic beam 88, generated by transducer 82, can provide therapy to a target 86 in tissue 63. Prior to introducing acoustic device 80 into the body cavity, an acoustic coupler 60 is attached to the acoustic device. Acoustic coupler 60 similarly includes a liquid chamber 62, a pouch 64, a liquid inlet 66, and a liquid outlet 68. Significantly, dimensions of pouch 64 have been selected such that substantially the entire mass of a distal end of acoustic device 80 (including transducer 82) can be introduced into pouch 64. As is illustrated by FIG. 5B, acoustic coupler 60 includes a surface 70, which both defines the open-ended volume of pouch 64, and is configured to conform to the shape and size of transducer 82. Acoustic coupler 60 also includes a surface 72, which both defines an outer extent of the acoustic coupler and is configured to conform to tissue 63. Pouch 64 can be configured to achieve an interference fit with the distal end of acoustic device 80. Particularly when used as indicated in FIG. 5A, inflation of liquid chamber 62 should secure the acoustic coupler to the acoustic device, as well as securing the combination of the acoustic coupler and the acoustic device in the body cavity, even when the dimensions of the pouch are not sufficient to achieve an interference fit.

FIG. 6 is a chart illustrating the performance of empirical acoustic couplers generally consistent with acoustic coupler 10 of FIG. 1A (labeled "opposite" in FIG. 6) and acoustic coupler 10a of FIG. 2A (labeled "adjacent" in FIG. 6). Both configurations of acoustic couplers were able to remove the heat generated by either a 3.5 MHz transducer or a 5.0 MHz transducer.

FIG. 7 graphically illustrates the percentage of heat removed by an acoustic coupler (including a liquid chamber) relative to a focal depth of the transducer, indicating that increasing flow rates enable higher percentages of heat to be removed.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. An acoustic coupler adapted to be disposed between an acoustic transducer and a physical mass to acoustically couple the acoustic transducer with the physical mass, the acoustic coupler comprising:
   a liquid chamber, the liquid chamber including—
      a liquid inlet configured to be coupled in fluid communication with a supply volume for holding a circulating liquid;
      a liquid outlet configured to be coupled in fluid communication with a discharge volume for the circulating liquid;
      a first surface configured to conform to the acoustic transducer; and
      a second surface configured to conform to the physical mass; and a pouch coupled with the liquid chamber, the pouch being configured to removably secure the acoustic coupler to the acoustic transducer, the pouch comprising an open-ended volume configured to receive the acoustic transducer such that when the acoustic transducer is inserted into the open ended volume, the first surface of the acoustic coupler conforms to the acoustic transducer, wherein the circulating liquid in the liquid chamber and the open-ended volume are separated by the first surface, the pouch being formed from a flexible elastomeric material configured to achieve an interference fit with the transducer.

2. The acoustic coupler of claim 1, wherein the acoustic coupler is formed of a biocompatible material.

3. The acoustic coupler of claim 1, wherein the acoustic coupler comprises polyurethane.

4. The acoustic coupler of claim 1 wherein a relative orientation of the liquid inlet and the liquid outlet has been selected to enhance a circulation of liquid through the liquid chamber.

5. The acoustic coupler of claim 1, wherein a relative orientation of the liquid inlet and the liquid outlet comprises an angular separation between the liquid inlet and the liquid outlet of between about 40 degrees and about 110 degrees.

6. The acoustic coupler of claim 1, further comprising a temperature sensor disposed in at least one of the liquid inlet, the liquid outlet, and the liquid chamber.

7. The acoustic coupler of claim 1 wherein the acoustic coupler is configured such that when the acoustic coupler is properly positioned relative to the acoustic transducer, the first surface of liquid chamber substantially encompasses the transducer.

8. The acoustic coupler of claim 1 wherein the first surface has a plurality of pores configured to release a portion of the circulating liquid in the liquid chamber to wet the first surface and thereby facilitate more efficiently acoustically coupling the acoustic coupler with the transducer.

9. The acoustic coupler of claim 1 wherein the second surface has a plurality of pores configured to release a portion of the circulating liquid in the liquid chamber to wet the second surface and thereby facilitate more efficiently acoustically coupling the acoustic coupler with the physical mass.

10. The acoustic coupler of claim 1 wherein the acoustic transducer is a high frequency ultrasound (HIFU) transducer, and wherein the first surface of the liquid chamber is configured to contact and conform to the HIFU transducer.

11. The acoustic coupler of claim 1 wherein the physical mass is a biological tissue, and wherein the second surface of the liquid chamber is configured to conform to the biological tissue.

12. An acoustic coupler adapted to be disposed between an ultrasound transducer and a physical mass to acoustically couple the ultrasound transducer with the physical mass, the acoustic coupler comprising:
having a first wall defining at least a portion of an open ended volume for removably receiving the ultrasound transducer such that when the ultrasound transducer is positioned in the open ended volume, the ultrasound transducer is substantially enveloped by the open ended volume, wherein the first wall is configured to conform to the ultrasound transducer, and wherein the liquid chamber further comprises—
a liquid inlet configured to be coupled in fluid communication with a supply volume for holding a circulating liquid;
a liquid outlet configured to be coupled in fluid communication with a discharge volume for the circulating liquid; and
a second wall substantially opposite the first wall and configured to conform to the physical mass.

13. The acoustic coupler of claim 12, wherein the open ended volume defined by the liquid chamber is configured to achieve an interference fit with the ultrasound transducer.

14. The acoustic coupler of claim 12 wherein the first wall of the liquid chamber is configured to contact and conform to a front face of the ultrasound transducer.

15. A system for acoustically coupling an ultrasound transducer with a physical mass, the system comprising:
an acoustic coupler comprising—
a liquid chamber including a liquid inlet configured to introduce a liquid into the liquid chamber, a liquid outlet configured to remove a liquid from the liquid chamber, a first surface configured to conform to the ultrasound transducer, and a second surface configured to conform to the physical mass; and
a pouch coupled to the liquid chamber, the pouch being configured to removably secure the acoustic coupler to the ultrasound transducer, the pouch having an open ended volume being configured to receive the ultrasound transducer such that when the ultrasound transducer is inserted into the open ended volume, the first surface of the liquid chamber conforms to the ultrasound transducer;
a liquid supply coupled in fluid communication with the liquid inlet;
a pump configured to at least partially fill the liquid chamber with a liquid and circulate the liquid through the system; and
a cooling unit coupled in fluid communication with the liquid supply such that the cooling unit cools the liquid being circulated through the system to cool the ultrasound transducer.

16. The system of claim 15, further comprising a degasser configured to remove gas bubbles from the liquid.

17. The system of claim 15, further comprising:
a first liquid line coupling the liquid supply with the liquid inlet;
a second liquid line coupled to the cooling unit, the first liquid line being relatively larger in size than the second liquid line.

18. The system of claim 15 wherein the first surface of the liquid chamber is configured to at least substantially separate liquid in the liquid chamber from the ultrasound transducer when the ultrasound transducer is positioned in the pouch.

19. A system for acoustically coupling an ultrasound transducer configured to emit acoustic energy with a physical mass, while providing cooling to the ultrasound transducer, the system comprising:
an acoustic coupler comprising a liquid chamber including:
a liquid inlet configured to introduce a liquid into the liquid chamber;
a liquid outlet configured to remove a liquid from the liquid chamber;
a first surface configured to conform to the ultrasound transducer; and
a second surface configured to conform to the physical mass,
wherein at least one of the first surface and the second surface includes a plurality of pores configured to release a portion of liquid from the liquid chamber to enhance coupling with at least one of the ultrasound transducer and the physical mass;

a liquid supply coupled in fluid communication with the liquid inlet;

a pump configured to fill the liquid chamber with the liquid that is used to acoustically couple the ultrasound transducer with the physical mass, and to circulate the liquid through the system;

a cooling unit coupled in fluid communication with the liquid supply, such that the cooling unit cools the liquid being circulated through the system to cool the ultrasound transducer; and a flow meter enabling a flow rate of liquid circulating through the system to be varied.

20. The system of claim 19, further comprising a degasser configured to remove gas bubbles from a liquid circulating through the system.

21. The system of claim 19, wherein the flow meter comprises:

a meter providing an indication of a current flow rate; and at least one valve for varying the flow rate.

22. The system of claim 19 wherein the liquid chamber defines an internal open ended volume for removably receiving the ultrasound transducer, such that when the acoustic coupler is properly positioned relative to the ultrasound transducer, the ultrasound transducer is substantially enveloped by the open ended volume, the open ended volume being separate from a fluid volume portion of the liquid chamber configured to accommodate the liquid introduced into the liquid chamber.

23. A system for acoustically coupling an ultrasound transducer configured to emit acoustic energy with a physical mass, while providing cooling to the ultrasound transducer, the system comprising:

an acoustic coupler comprising a liquid chamber including:

a liquid inlet configured to introduce a liquid into the liquid chamber;

a liquid outlet configured to remove a liquid from the liquid chamber;

a first surface configured to conform to the ultrasound transducer;

a second surface configured to conform to the physical mass, a pouch coupled to the liquid chamber, the pouch being configured to secure the acoustic coupler to the ultrasound transducer, the pouch comprising an open ended volume configured to receive the ultrasound transducer such that when the ultrasound transducer is inserted into the open ended volume, the first surface of the acoustic coupler conforms to the ultrasound transducer, the first surface forming a barrier between liquid in the liquid chamber and the open ended volume;

a liquid supply coupled in fluid communication with the liquid inlet;

a pump configured to fill the liquid chamber with the liquid that is used to acoustically couple the ultrasound transducer with the physical mass, and to circulate the liquid through the system;

a cooling unit coupled in fluid communication with the liquid supply, such that the cooling unit cools the liquid being circulated through the system to cool the ultrasound transducer; and a flow meter enabling a flow rate of liquid circulating through the system to be varied.

24. A method for acoustically coupling an ultrasound transducer with a physical mass, the method comprising:

inserting the ultrasound transducer into an open ended volume of an acoustic coupler, the acoustic coupler including a liquid chamber separated from the open ended volume by a first wall, the first wall at least substantially preventing liquid from the liquid chamber from entering the open ended volume, wherein the open ended volume is made from a flexible elastomeric material configured to achieve an interference fit with the ultrasound transducer for removably attaching the acoustic coupler to the ultrasound transducer;

positioning the liquid chamber between the physical mass and the ultrasound transducer;

introducing a liquid into the liquid chamber such that the first wall of the liquid chamber conforms to the ultrasound transducer and a second wall of the liquid chamber conforms to the physical mass; and introducing a circulating flow of the liquid through the liquid chamber, the flow of liquid absorbing heat from the ultrasound transducer to provide cooling to the ultrasound transducer.

25. The method of claim 24, further comprising releasing a portion of liquid in the liquid chamber via an opening in the first wall to facilitate acoustically coupling the first wall to the ultrasound transducer.

26. The method of claim 24, further comprising releasing a portion of liquid in the liquid chamber via an opening in the second wall to facilitate acoustically coupling the second wall to the physical mass.

27. The method of claim 24 wherein inserting the ultrasound transducer into the open ended volume of the acoustic coupler further comprises contacting a front face of the ultrasound transducer with the first wall of the liquid chamber.

* * * * *

UNITED STATES PATENT AND TRADEMARK OFFICE
CERTIFICATE OF CORRECTION

PATENT NO. : 8,611,189 B2
APPLICATION NO. : 11/229005
DATED : December 17, 2013
INVENTOR(S) : Shahram Vaezy et al.

It is certified that error appears in the above-identified patent and that said Letters Patent is hereby corrected as shown below:

On the Title Page, Item (56)

In column 2, under "Other Publications", line 1, delete "prescence" and insert -- presence --, therefor.

On page 3, in column 1, under "Other Publications", line 50, delete "Vivo" and insert -- Vitro --, therefor.

On page 3, in column 1, under "Other Publications", line 50, delete "Interial" and insert -- Inertial --, therefor.

On page 3, in column 1, under "Other Publications", line 61, delete "Aikoy," and insert -- Aikou, --, therefor.

On page 3, in column 2, under "Other Publications", line 6, delete "Ahesion" and insert -- Adhesion --, therefor.

On page 3, in column 2, under "Other Publications", line 19, delete "Nonivasive" and insert -- Noninvasive --, therefor.

On page 3, in column 2, under "Other Publications", line 39, delete "Investigation" and insert -- Investigations --, therefor.

On page 3, in column 2, under "Other Publications", line 59, delete "Netwowk," and insert -- Network, --, therefor.

On page 3, in column 2, under "Other Publications", line 62, delete "Ultrsound," and insert -- Ultrasound, --, therefor.

On page 4, in column 1, under "Other Publications", line 1, delete "of" and insert -- of a --, therefor.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,611,189 B2

On page 4, in column 2, under "Other Publications", line 35, Delete "Ophthamology," and insert -- Ophthalmology, --, therefor.

In the Claims

In column 13, line 44, In Claim 23, Delete "mass," and insert -- mass; and --, therefor.